US006187770B1

(12) United States Patent
Jørgensen et al.

(10) Patent No.: US 6,187,770 B1
(45) Date of Patent: Feb. 13, 2001

(54) N-SUBSTITUTED AZAHETEROCYCLIC COMPOUNDS

(75) Inventors: Tine Krogh Jørgensen, Herlev; Rolf Hohlweg, Kvistgaard; Knud Erik Andersen, Brøndby; Uffe Bang Olsen, Vallensbæk, all of (DK); Zdeněk Polivka; Karel Sindelar, both of Prague (CS)

(73) Assignee: Novo Nordisk A/S, Bagsværd (DK)

( * ) Notice: Under 35 U.S.C. 154(b), the term of this patent shall be extended for 0 days.

(21) Appl. No.: 09/267,302

(22) Filed: Mar. 15, 1999

Related U.S. Application Data
(60) Provisional application No. 60/079,056, filed on Mar. 23, 1998.

(30) Foreign Application Priority Data
Mar. 17, 1998 (DK) .................................................... 0367/98

(51) Int. Cl.$^7$ ...................... A61K 31/395; C07D 267/12; C07D 281/08; A61P 25/04; A61P 29/00
(52) U.S. Cl. ........................................ 514/211.1; 540/546
(58) Field of Search .......................... 540/546; 514/211.1

(56) References Cited
U.S. PATENT DOCUMENTS
3,701,778  10/1972  van der Burg ...................... 260/268
5,049,637 * 9/1991  Copp et al. ............................ 528/44

FOREIGN PATENT DOCUMENTS
0 421823 A2  4/1991  (EP) .

WO 88/07997  10/1988  (WO) .

* cited by examiner

Primary Examiner—Mukund J. Shah
Assistant Examiner—Brenda Coleman
(74) Attorney, Agent, or Firm—Steve T. Zelson, Esq.; Carol E. Rozek, Esq.

(57) ABSTRACT

The present invention relates to novel N-substituted azaheterocyclic compounds of the general formula

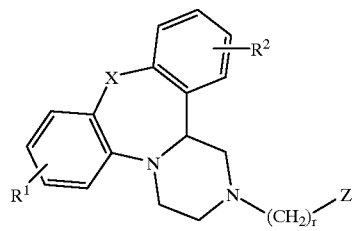

wherein X, Z, $R^1$, $R^2$ and r are as defined in the detailed part of the present description, or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation, as well as their use for treatment of indications caused by or related to the secretion and circulation of insulin antagonising peptides, e.g. non-insulin-dependent diabetes mellitus (NIDDM) and ageing-associated obesity.

19 Claims, No Drawings

N-SUBSTITUTED AZAHETEROCYCLIC COMPOUNDS

CROSS-REFERENCE TO RELATED APPLICATIONS

This application claims priority under 35 U.S.C. 119 of Danish application 0367/98 filed Mar. 17, 1998, and of U.S. provisional application 60/079,056 filed Mar. 23, 1998, the contents of which are fully incorporated herein by reference.

FIELD OF INVENTION

The present invention relates to novel N-substituted azaheterocyclic compounds or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for the treatment of non-insulin-dependent diabetes mellitus (NIDDM), insulin resistance as well as ageing-associated obesity, the present compounds being known to interfere with neuropeptide containing C-fibres and hence to inhibit the secretion and circulation of insulin antagonising peptides like CGRP or amylin.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastrointestinal diseases or migraine.

Furthermore, the fact that the C-fibers innervate the liver, the intestines and the pancreas suggests that they control various function. The peptidergic innervation has been shown to control glucose tolerance in rodents (Karlsson et al. Am. J. Physiol. 267, R1071–R1077, 1994, Guillot et al. Life Sci. 969–977, 1996).

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

A number of tetracyclic piperazino-azepines, including mianserin which may be used in the treatment of depression, are known in the literature. In EP 421823 and 539164 tetracyclic dibenzo-pyrazino-azepines and benzo-pyrido-pyrazino-azepines are described as having anti-allergic and anti-asthmatic activites. Further, EP 447857 discloses inter alia tetracyclic dibenzo-pyrazino-azepines as anti-allergic anti-asthistaminic agents and agents for bronchial asthma.

SUMMARY OF THE INVENTION

The present invention relates to compounds of the general formula I wherein X, Z, $R^1$, $R^2$ and r are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, neurogenic inflammation, migraine, neuropathy, itching and rheumatoid arthritis, as well as indications caused by or related to the secretion and circulation of insulin antagonising peptides and other peptides derived from the sensory nervous system, e.g. non-insulin-dependent diabetes mellitus (NIDDM), insulin resistance and ageing-associated obesity.

In another aspect, the present invention includes within its scope pharmaceutical compositions comprising, as an active ingredient, at least one of the compounds of the general formulae or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, neurogenic inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM), insulin resistance and ageing-associated obesity.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, neurogenic inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM), insulin resistance and ageing-associated obesity.

Further objects will become apparent from the following description.

DETAILED DESCRIPTION OF THE INVENTION

Accordingly, the present invention relates to novel N-substituted azaheterocyclic compounds of the general formula I

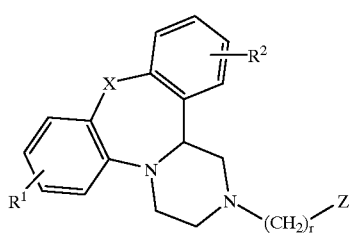

wherein $R^1$ and $R^2$ independently are hydrogen, halogen, trifluoromethyl, hydroxy, $C_{1-6}$-alkyl or $C_{1-6}$-alkoxy; and X is —O—, —S— or —S(=O)—; and r is 0, 1, 2, 3, 4, 5, 6, 7, 8, 9 or 10; and Z is selected from

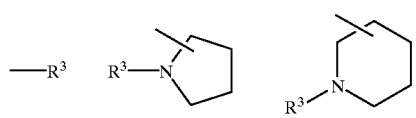

wherein $R^3$ is —$(CH_2)_m$OH or —$(CH_2)_p COR^4$ wherein m and p independently are 0, 1, 2, 3 or 4 and $R^4$ is OH, $NH_2$, NHOH or $C_{1-6}$-alkoxy; or a pharmaceutically acceptable salt thereof.

The compounds according to the invention may exist as geometric and optical isomers and all isomers, as separeted, pure or partially purified stereoisomers or racemic mixtures thereof are included in the scope of the invention. Isomers may be separated by means of standard methods such as chromatographic techniques or fractional crystallisation of suitable salts.

Preferably, the compounds according to the invention exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds according to the invention may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms. Typical $C_{1-6}$-alkyl groups include, but are not limited to, methyl, ethyl, n-propyl, iso-propyl, n-butyl, sec-butyl, iso-butyl, tert-butyl, n-pentyl, iso-pentyl, 2-methylbutyl, 3-methylbutyl, n-hexyl, iso-hexyl, 4-methylpentyl, neopentyl, 1,2-dimethylpropyl, 2,2-dimethylpropyl, 1,2,2-trimethylpropyl and the like.

The term "$C_{1-6}$alkoxy" as used herein, alone or in combination is intended to include those $C_{1-6}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "halogen" means fluorine, chlorine, bromine or iodine.

In a preferred embodiment of the invention $R^1$ and $R^2$ are selected from hydrogen, halogen, trifluoromethyl or $C_{1-6}$-alkyl. Preferably $R^1$ and $R^2$ are hydrogen.

In another preferred embodiment of the invention X is —O— or —S—.

In another preferred embodiment of the invention r is 0, 1, 2, 3 or 4.

In another preferred embodiment of the invention Z is —$R^3$.

In another preferred embodiment of the invention $R^3$ is —$(CH_2)_p COR^4$ wherein p is 0, 1, 2 or 3.

In yet another preferred embodiment of the invention $R^4$ is OH.

Preferred compounds of the present invention include:
4-(1,3,4,14b-Tetrahydro-2H-dibenzo[b,f]pyrazino[1,2-d][1,4]oxazepin-2-yl)-butanoic acid;
4-(1,3,4,14b-Tetrahydro-2H-dibenzo[b,f]pyrazino[1,2-d][1,4]thiazepin-2-yl)-butanoic acid;
or a pharmaceutically acceptable salt thereof.

Further preferred compounds of the present invention include:
5-(1,3,4,14b-Tetrahydro-2H-dibenzo[b,f]pyrazino[1,2-d][1,4]thiazepin-2-yl)-pentanoic acid;
3-(1,3,4,14b-Tetrahydro-2H-dibenzo[b,f]pyrazino[1,2-d][1,4]thiazepin-2-yl)-propionic acid;
5-(1,3,4,14b-Tetrahydro-2H-dibenzo[b,f]pyrazino[1,2-d][1,4]oxazepin-2-yl)-pentanoic acid;
3-(1,3,4,14b-Tetrahydro-2H-dibenzo[b,f]pyrazino[1,2-d][1,4]oxazepin-2-yl)-propionic acid;
or a pharmaceutically acceptable salt thereof.

It has been demonstrated that the compounds according to the invention inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the compounds according to the invention exhibit a potent inhibitory effect. The compounds according to the invention may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I lower the glucose levels in diabetic rodents (ob/ob mice and diabetic fat Zucker rats) as well as improve the glucose tolerance and that this may result from the reduced release of CGRP from peripheral nervous endings and other peptides derived from the sensory nervous system. Hence the compounds of general formula I may be used in the treatment of NIDDM, insulin resistance as well as ageing-associated obesity. Experimentally this can be demonstrated by the administration of histamine chloride icv into NMRI mice with previous treatment ip of a compound of formula I.

The compounds of formula I may be prepared by the following method:

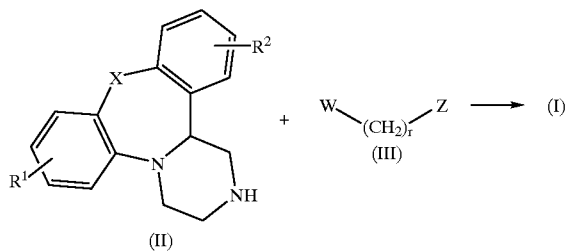

A compound of formula II wherein $R^1$, $R^2$ and X are as defined above may be reacted with a compound of formula III wherein r and Z are as defined above and W is a suitable leaving group such as halogen, p-toluene sulphonate or mesylate, to form a compound of formula I. This alkylation reaction may be carried out in a solvent such as dimethylsulfoxide, N,N-dimethylformamide, acetone, dibutylether, 2-butanone, tetrahydrofuran (THF), dioxane or toluene in the presence of a base e.g. sodium hydride or potassium carbonate and a catalyst, e.g. an alkali metal iodide at a temperature up to reflux temperature for the solvent used for e.g. 1 to 120 h. If esters have been prepared in which $R^4$ is alkoxy, compounds of formula I wherein $R^4$ is OH may be prepared by hydrolysis of the ester group, prefarably at room temperature in a mixture of an aqueous alkali metal hydroxide and an alcohol such as methanol or ethanol, for e.g. about 0.5 to 48 h.

Compounds of formulas II and III may readily be prepared by methods familiar to those skilled in the art.

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Histamine Induced Hyperglycemia in Mice

Conscious unfasted 25 g male NMRI mice are administered histamine chloride (90 nmol) icv according to the method of Nishibori et al. (J. Pharmacol. Exp. Therap. 241, 582–286, 1987). Blood glucose is determined at time 0 and 40 min after the histamine injection. Test compounds are administered at 1.0 mg/kg ip 30 min before the histamine injection, and % inhibition refers to the capacity of the compounds to inhibit the histamine induced blood glucose rise.

III. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced hyperglycemia for a representative compound is listed in table II.

TABLE I

| Inhibition of histamine induced hyperglycemia at 1.0 mg/kg | |
|---|---|
| Example no. | % inhibition |
| 04 | 48 |

PHARMACEUTICAL COMPOSITIONS

The present invention also relates to pharmaceutical compositions comprising, as an active ingredient, at least one of the compounds of the general formulas or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in *Remington: The Science and Practise of Pharmacy*, 19th Ed., 1995. The compositions may appear in conventional forms, for example capsules, tablets, aerosols, solutions, suspensions or topical applications.

Typical compositions include a compound of the general formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, inflammation, diabetic neuropathy and rheumatoid arthritis, as well as indications caused by or related to the secretion and circulation of insulin antagonising peptides, such as non-insulin-dependent diabetes mellitus (NIDDM), insulin resistance or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds of the invention are effective over a wide dosage range. For example, in the treatment of humans, dosages from about 0.5 to about 1000 mg, preferably from about 1 to about 500 mg of compounds of the present invention, conveniently given from 1 to 5 times daily. A most preferable dosage is from about 50 to about 200 mg per dose when administered to e.g. a human. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 50 to about 200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

The method of treating may be described as the treatment of an indication caused by or related to the secretion and circulation of insulin antagonising peptides like CGRP or amylin in a subject in need thereof, which comprises the step of administering to the said subject a neurologically effective amount of a compound of the invention, or a pharmaceutically acceptable salt thereof.

Any novel feature or combination of features described herein is considered essential to this invention.

EXAMPLES

The process for preparing compounds of the present invention and preparations containing them is further illustrated in the following examples, which, however, are not to be construed as limiting.

Hereinafter, TLC is thin layer chromatography, CDCl$_3$ is deuterio chloroform and DMSO-d$_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta^H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

4-(1,3,4,14b-Tetrahydro-2H-dibenzo[b,f]pyrazino[1,2-d][1,4]oxazepin-2-yl)-butanoic acid hydrochloride

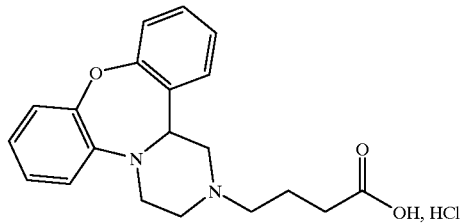

A solution of 2-methyl-(1,3,4,14b-tetrahydro-2H-dibenzo[b,f]pyrazino[1,2-d][1,4]oxazepine) (2.0 g, 7.5 mmol, prepared similarly as described in Neth. Appl. 6709520, Chem. Abs. 70, 115192 (1969)) in toluene (12 ml) was added drop wise to a stirred solution of ethyl chloroformate (1.26 g, 1.1 ml, 11.7 mmol) in toluene (8 ml) at 60° C. The mixture was heated at reflux temperature for 2 h. After cooling, the mixture was washed with a saturated solution of sodium bicarbonate (2×10 ml), water (10 ml), dried (MgSO$_4$) and evaporated. The residue (2.5 g) was purified by column chromatography on silica gel (50 g) using benzene as eluent to give 1.95 g (80%) of 2-ethoxycarbonyl-(1,3,4,14b-tetrahydro-2H-dibenzo[b,f]pyrazino[1,2-d][1,4]oxazepine) as an oil.

TLC: R$_f$=0.25 (SiO$_2$: chloroform/benzene=1:4).

A mixture of the above carbamate (1.9 g, 5.9 mmol), potassium hydroxide (1.2 g) and ethanol (2 ml) was stirred and heated for 3.5 h at reflux temperature. The solidified mixture was dissolved in water (20 ml) and the mixture was extracted with dichloromethane (3×15 ml). The combined extracts were washed with water, brine, dried (K$_2$CO$_3$) and evaporated in vacuo. The residue was crystallized from mixture of benzene and n-hexane. This afforded 1.1 g (75%) 1,3,4,14b-tetrahydro-2H-dibenzo-[b,f]pyrazino[1,2-d][1,4] oxazepine.

To a solution of the above oxazepine (1.1 g, 4.4 mmol) in dimethyl sulfoxide (11 ml), ethyl 4-chlorobutyrate (1.14 g, 5.45 mmol), potassium carbonate (0.9 g, 6.5 mmol) and sodium iodide (0.32 g) were added and the reaction mixture was heated at 60–70° C. for 5 h and then left to stand overnight. The reaction mixture was diluted with benzene (70 ml), the precipitated solid was filtered off and washed with benzene (2×10 ml), and the filtrate was washed with water (5×15 ml). The benzene solution was dried (MgSO$_4$) and the solvent was evaporated in vacuo. The residue (2.4 g) was purified by column chromatography on silica gel (60 g) using chloroform as eluent. This afforded 1.72 g (93%) of 4-(1,3,4,14b-tetrahydro-2H-dibenzo[b,f]pyrazino[1,2-d][1,4]oxazepin-2-yl)butyric acid ethyl ester as an oil.

TLC: R$_f$=0.52 (SiO$_2$: chloroform).

A mixture of the above ethyl ester (1.7 g, 4.0 mmol), 4 N sodium hydroxide (9 ml) and ethanol (15 ml) was stirred at room temperature for 3 h and left overnight. The reaction mixture was then poured into dichloromethane (200 ml) and acidified with concentrated hydrochloric acid to pH 1. The dichloromethane layer was separated, washed with water (10 ml), dried (MgSO$_4$) and evaporated in vacuo. The oily residue was re-evaporated twice with acetone and then triturated with hot acetone. The precipitate was filtered off, washed with acetone and dried. This afforded 0.85 g (57%) of the title compound as a solid.

M.p. 223–232° C.; Calculated for C$_{20}$H$_{22}$N$_2$O$_3$, HCl, 0.25 H$_2$O: C, 63.32%; H, 6.24%; N, 7.38%; Cl, 9.35%; Found: C, 63.46%; H, 6.27%; N, 7.14%; Cl, 9.33%.

Example 2

4-(1,3,4,14b-Tetrahydro-2H-dibenzo[b,f]pyrazino[1,2-d][1,4]thiazepin-2-yl)butyric acid hydrogen oxalate

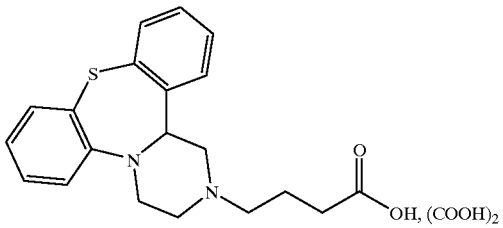

A mixture of 1,3,4,14b-tetrahydro-2H-dibenzo[b,f]pyrazino[1,2-d][1,4]thiazepine (2.8 g, 10.4 mmol, prepared similarly as described in Neth. 6709520, Chem Abstr. 70, 115192 (1969)), ethyl 4-chlorobutyrate (3.0 g, 20 mmol), potassium carbonate (2.2 g, 16 mmol), sodium iodide (1.5 g, 10 mmol) and acetone (100 ml) was heated under stirring at reflux temperature for 14 h. The inorganic salts were filtered off and the filtrate was evaporated in vacuo to give a residue which was purified by chromatography on silica gel (50 g) using ethyl acetate as eluent. This afforded 2.7 g (68%) of 4-(1,3,4,14b-tetrahydro-2H-dibenzo[b,f]pyrazino[1,2-d][1,4]thiazepin-2-yl)butyric acid ethyl ester as an oil.

TLC: R$_f$=0.61 (SiO$_2$: chloroform/ethanol/ammonia= 20:1:0.05).

The above ester (2.70 g, 7.1 mmol) was dissolved in ethanol (40 ml) and 20% sodium hydroxide (5 ml) was added. The mixture was allowed to stand for 7 days at room temperature, the ethanol was evaporated in vacuo and water (20 ml) was added. The mixture was extracted with diethyl ether and the phases were separated. Acetic acid (4 ml) was added to the water phase and the product was extracted with dichloromethane (50 ml). The organic phase was dried (MgSO$_4$) and the solvent was evaporated in vacuo. The residue was dissolved in acetone and treated with a solution of oxalic acid dihydrate in acetone. This afforded after filtration and drying 2.36 g (73%) of the title compound.

M.p. 214–216° C.; Calculated for C$_{20}$H$_{22}$N$_2$O$_2$S, C$_2$H$_2$O$_4$, 0.75 H$_2$O: C, 57.69%; H, 5.61%; N, 6.12%; S, 7.00%; Found: C, 57.59%; H, 5.29%; N, 5.97%; S, 6.96%.

Example 3
5-(1,3,4,14b-Tetrahydro-2H-dibenzo[b,f]pyrazino[1,2-d][1,4]thiazepin-2-yl)-pentanoic acid

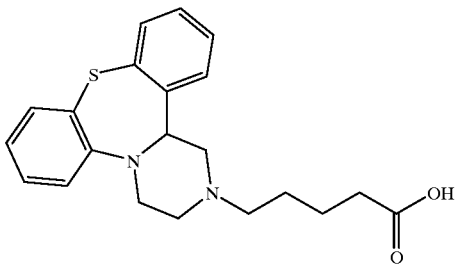

A mixture of 1,3,4,14b-tetrahydro-2H-dibenzo[b,f]pyrazino[1,2-d][1,4]thiazepine (1.37 g, 5.1 mmol, preparred similarly as described in Neth. 6709520, C.A. 70, 115192 (1969)), ethyl 5-bromopentanoate (1.77 g, 8.5 mmol), potassium carbonate (1.45 g, 10.5 mmol) and acetone (40 ml) was heated under stirring at reflux temperature for 14 h. The mixture was filtered and the filtrate was evaporated in vacuo. The residue was purified by chromatography on silica gel (50 g) using ethyl acetate as eluent. This afforded 1.95 g (96%) of 5-(1,3,4,14b-tetrahydro-2H-dibenzo[b,f]pyrazino[1,2-d][1,4]thiazepin-2-yl)pentanoic acid ethyl ester as an oil.

TLC: $R_f$=0.54 (SiO$_2$: chloroform/ethanol/ammonia=20:1:0.05).

The above ester (1.95 g, 4.9 mmol) was dissolved in ethanol (30 ml) and 20% sodium hydroxide (3 ml) was added. The mixture was allowed to stand for 7 days at room temperature, ethanol was evaporated in vacuo and water (20 ml) was added. The mixture was extracted with diethyl ether and the phases were separated. Acetic acid (2 ml) was added to the aqueous phase and the solid was filtered off. Re-crystallisation of the solid from ethanol yielded 1.52 g (73%) of the title compound as crystals.

M.p. 226–230° C.; Calculated for $C_{21}H_{24}N_2O_2S$, ¼ $H_2O$: C, 67.62%; H, 6.62%; N, 7.51%; S, 8.60%; Found: C, 68.02%; H, 6.56%; N, 7.50%; S, 8.29%.

Example 4
3-(1,3,4,14b-Tetrahydro-2H-dibenzo[b,f]pyrazino[1,2-d][1,4]thiazepin-2-yl)-propionic acid

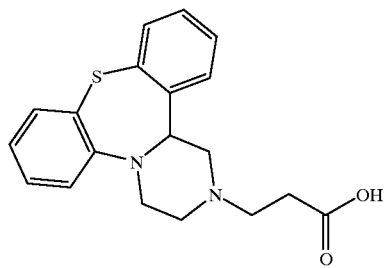

A mixture of 1,3,4,14b-tetrahydro-2H-dibenzo[b,f]pyrazino[1,2-d][1,4]thiazepine (1.5 g, 5.6 mmol), ethyl acrylate (0.61 g, 6.1 mmol) and ethanol (40 ml) was heated at reflux temperature for 5 minutes and then left to stand for 24 h at room temperature, affording crude 3-(1,3,4,14b-tetrahydro-2H-dibenzo[b,f]pyrazino[1,2-d][1,4]thiazepin-2-yl)propionic acid ethyl ester.

To the above crude mixture 20% sodium hydroxide (3 ml) was added, and the solution was left standing for 7 days. Ethanol was evaporated in vacuo and water (20 ml) was added. The mixture was extracted with diethyl ether (20 ml) and the phases were separated. Acetic acid (2 ml) was added to the aqueous phase and the solid was filtered off. Crystallisation from ethanol yielded 1.67 g (88%) of the title compound as crystals.

M.p. 218–220° C. Calculated for $C_{19}H_{20}N_2O_2S$, 1½ $H_2O$: C, 62.10%; H, 6.31%; N, 7.62%; S, 8.73%; Found: C, 62.32%; H, 6.53%; N, 7.61%; S, 8.79%.

Example 5
5-(1,3,4,14b-Tetrahydro-2H-dibenzo[b,f]pyrazino[1,2-d][1,4]oxazepin-2-yl)-pentanoic acid hydrochloride

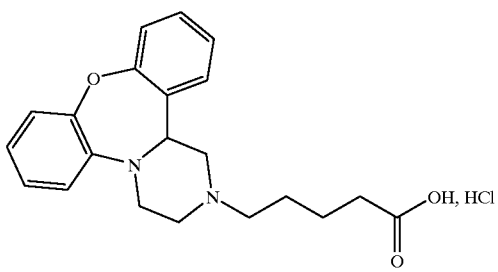

Ethyl 5-bromopentanoate (1.66 g, 0.0079 mol) and potassium carbonate (1.75 g, 0.0127 mol) were added to a solution of 1,3,4,14b-tetrahydro-2H-dibenzo[b,f]pyrazino[1,2-d][1,4]-oxazepine (1.6 g, 0.0063 mol prepared similarly as described in Neth. Appl. 6709520, Chem. Abs. 70, 115192 (1969)) in 2-butanone (45 ml) and the reaction mixture was heated at 70–80° C. for 17 h. The mixture was diluted with benzene (50 ml), the solid was filtered off, washed with benzene (2×10 ml) and the filtrate was evaporated in vacuo. The residue (3.2 g) was purified by column chromatography on silica gel (100 g) using benzene and a mixture of benzene and chloroform (1:1) as eluents to afford 2.35 g (97%) crude 5-(1,3,4,14b-tetrahydro-2H-dibenzo[b,f]-pyrazino[1,2-d][1,4]oxazepin -2-yl)pentanoic acid ethyl ester.

TLC: $R_f$=0.32 (SiO$_2$: chloroform).

The crude base was dissolved in diethyl ether (40 ml) and treated with oxalic acid (0.895 g) in ethanol (2 ml). Crystalline hydrogen oxalate was filtered off and recrystallised from a mixture of 96% ethanol (40 ml) and diethyl ether (40 ml). This yielded 2.33 g (78%) of 5-(1,3,4,14b-tetrahydro-2H-dibenzo[b,f]pyrazino[1,2-d][1,4]oxazepin-2-yl) pentanoic acid ethyl ester hydrogen oxalate.

A mixture of the above ethyl ester (2.0 g, 0.005 mol), 15% sodium hydroxide (7 ml) and ethanol (10 ml) was stirred at room temperature for 3 h and left stirring overnight. The reaction mixture was then poured into dichloromethane (150 ml) and acidified with concentrated hydrochloric acid to pH 1. The organic phase was separated, washed with water (10 ml), dried (MgSO$_4$) and evaporated in vacuo. The oily residue was re-evaporated twice with acetone and then triturated with hot acetone (20 ml). The solid was filtered off, washed with acetone and dried. This afforded the title compound as a crystalline solid (1.67 g, 82%).

M.p. 221–226° C.; Calculated for $C_{21}H_{24}N_2O_2$, HCl: C, 64.86%; H, 6.48%; N, 7.20%; Cl, 9.12%; Found: C, 65.03%; H, 6.71%; N, 7.06%; Cl, 8.83%.

Example 6
3-(1,3,4,14b-Tetrahydro-2H-dibenzo[b,f]pyrazino[1,2-d][1,4]oxazepin-2-yl)-propionic acid hydrochloride

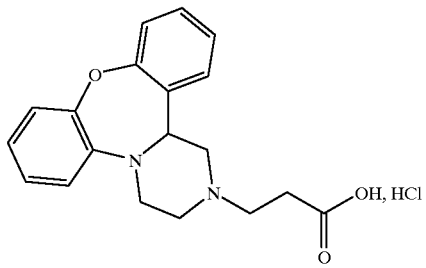

A mixture of 1,3,4,14b-tetrahydro-2H-dibenzo[b,f]pyrazino[1,2-d][1,4]oxazepine (1.3 g, 0.00515 mol) and ethyl acrylate (0.64 g, 0.00644 mol) in ethanol (30 ml) was heated at 70° C. for 3 h. The mixture was evaporated in vacuo and the residue was neutralised with a solution of oxalic acid (0.63 g) in ethanol (2 ml). Precipitated hydrogen oxalate was filtered off and recrystallised from a mixture of abs. ethanol (55 ml) and ether (50 ml). This afforded 1.58 g (69%) of 3-(1,3,4,14b-tetrahydro-2H-dibenzo[b,f]pyrazino[1,2-d][1,4]oxazepin-2-yl)propionic acid ethyl ester hydrogen oxalate as a crystalline solid.

The above ester (base liberated from hydrogen oxalate, 1.26 g, 0.00357 mol) was dissolved in ethanol (9 ml) and 15% sodium hydroxide (5 ml) was added. The reaction mixture was stirred at room temperature for 3 and left standing overnight. The reaction mixture was poured into dichloromethane (150 ml) and acidified with concentrated hydrochloric acid to pH 1. The dichloromethane layer was separated, washed with water (10 ml), dried (MgSO$_4$) and evaporated in vacuo. The oily residue was re-evaporated twice with acetone and then triturated with hot acetone (20 ml). This afforded the title compound as a crystalline solid (0.87 g, 68%).

M.p. 192–196° C.; Calculated for $C_{19}H_{20}N_2O_3$, HCl: C, 63.24%; H, 5.87%; N, 7.76%; Cl, 9.83%; Found: C, 63.12%; H, 6.04%; N, 7.69%; Cl, 9.86%.

What is claimed is:

1. A compound of formula I

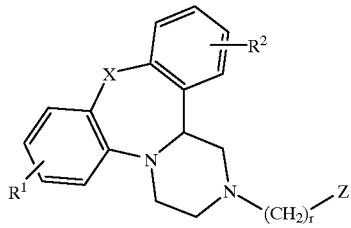

(I)

wherein $R^1$ and $R^2$ independently are hydrogen, halogen, trifluoromethyl, hydroxy, $C_{1-6}$-alkyl or $C_{1-6}$-alkoxy; and
X is —O—, —S— or —S(=O)—; and
r is 0, 1, 2, 3, 4, 5, 6, 7, 8, 9 or 10; and
Z is selected from

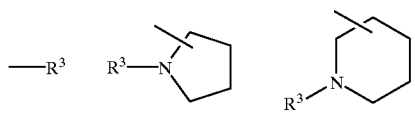

wherein $R^3$ is —(CH$_2$)$_m$OH or —(CH$_2$)$_p$COR$^4$ wherein m and p independently are 0, 1, 2, 3 or 4 and R$^4$ is OH, [NH$_2$, NHOH] or $C_{1-6}$-alkoxy; or a pharmaceutically acceptable salt thereof.

2. A compound according to claim 1 wherein $R^1$ and $R^2$ are selected from hydrogen, halogen, trifluoromethyl or $C_{1-6}$-alkyl.

3. A compound according to claim 1 wherein X is —O— or —S—.

4. A compound according to claim 1 wherein r is 0, 1, 2, 3 or 4.

5. A compound according to claim 1 wherein Z is —R$^3$.

6. A compound according to claim 1 wherein R$^3$ is —(CH$_2$)$_p$COR$^4$ wherein p is 0, 1, 2 or 3.

7. A compound according to claim 1 wherein R$^4$ is OH.

8. A compound selected from the following:
 4-(1,3,4,14b-Tetrahydro-2H-dibenzo[b,f]pyrazino[1,2-d][1,4]oxazepin-2-yl)-butanoic acid;
 4-(1,3,4,14b-Tetrahydro-2H-dibenzo[b,f]pyrazino[1,2-d][1,4]thiazepin-2-yl)-butanoic acid;
 or a pharmaceutically acceptable salt thereof.

9. A compound selected from the following:
 5-(1,3,4,14b-Tetrahydro-2H-dibenzo[b,f]pyrazino[1,2-d][1,4]thiazepin-2-yl)-pentanoic acid;
 3-(1,3,4,14b-Tetrahydro-2H-dibenzo[b,f]pyrazino[1,2-d][1,4]thiazepin-2-yl)-propionic acid;
 5-(1,3,4,14b-Tetrahydro-2H-dibenzo[b,f]pyrazino[1,2-d][1,4]oxazepin-2-yl)-pentanoic acid;
 3-(1,3,4,14b-Tetrahydro-2H-dibenzo[b,f]pyrazino[1,2-d][1,4]oxazepin-2-yl)-propionic acid;
 or a pharmaceutically acceptable salt thereof.

10. A pharmaceutical composition comprising as active component a compound according to claim 1 together with a pharmaceutically carrier or diluent.

11. The pharmaceutical composition according to claim 10 comprising between 0.5 mg and 1000 mg of the compound per unit dose.

12. A method of treating neurogenic pain or inflammation comprising administering to a subject in need thereof an effective amount of a compound according to claim 1.

13. A method of treating neurogenic pain or inflammation comprising administering to a subject in need thereof a pharmaceutical composition according to claim 10.

14. A method of treating neurogenic pain or inflammation associated with neuropathy, rheumatoid arthritis, migraine or itching, comprising administering to a subject in need thereof an effective amount of a compound according to claim 1.

15. A method of treating neurogenic pain or inflammation associated with neuropathy, rheumatoid arthritis, migraine or itching, comprising administering to a subject in need thereof a pharmaceutical composition according to claim 10.

16. A method of treating non-insulin-dependent diabetes mellitus (NIDDM) comprising administering to a subject in need thereof an effective amount of a compound according to claim 1.

17. A method of treating non-insulin-dependent diabetes mellitus (NIDDM) comprising administering to a subject in need thereof a pharmaceutical composition according to claim 10.

18. A method of treating insulin resistance comprising administering to a subject in need thereof an effective amount of a compound according to claim 1.

19. A method of treating insulin resistance comprising administering to a subject in need thereof a pharmaceutical composition according to claim 10.

* * * * *

UNITED STATES PATENT AND TRADEMARK OFFICE
CERTIFICATE OF CORRECTION

| | |
|---|---|
| PATENT NO. : 6,187,770 B1 | Page 1 of 1 |
| DATED : February 13, 2001 | |
| INVENTOR(S) : Jorgensen et al. | |

It is certified that error appears in the above-identified patent and that said Letters Patent is hereby corrected as shown below:

<u>Column 14,</u>
Line 1, please delete "[NH$_2$, NHOH].

Signed and Sealed this

Twenty-third Day of October, 2001

Attest:

*Nicholas P. Godici*

NICHOLAS P. GODICI
*Attesting Officer*     *Acting Director of the United States Patent and Trademark Office*